United States Patent [19]

Takeshita et al.

[11] Patent Number: 5,627,050
[45] Date of Patent: May 6, 1997

[54] BONE-RELATED SULFATASE-LIKE PROTEIN AND PROCESS FOR ITS PRODUCTION

[75] Inventors: Sunao Takeshita, Tokorozawa; Toshimi Ito, Sayama; Yoko Otawara-Hamamoto, Kamifukuoka; Egon Amann, Tokyo, all of Japan

[73] Assignee: Hoechst Japan Limited, Tokyo, Japan

[21] Appl. No.: 445,586

[22] Filed: May 22, 1995

Related U.S. Application Data

[63] Continuation of Ser. No. 111,887, May 26, 1993, abandoned.

[30] Foreign Application Priority Data

Aug. 28, 1992 [JP] Japan .................. 4-230030
Dec. 3, 1992 [JP] Japan .................. 4-324034

[51] Int. Cl.$^6$ .................. C12P 21/02; C12N 9/16
[52] U.S. Cl. .................. 435/69.1; 435/196; 530/350
[58] Field of Search .................. 435/196, 70.3, 435/71.1, 71.2, 69.1; 530/350

[56] References Cited

FOREIGN PATENT DOCUMENTS

0456229A2  11/1991  European Pat. Off. .

OTHER PUBLICATIONS

Meikle, M.C., The Distribution And Function Of Lysosomes In Conylar Cartilage, Journal of Anatomy, vol. 119, Part 1, pp. 85–96, Feb. 1975.
Purohit, A. et al., Estrogen Synthesis By Osteoblast Cell Lines, Endocrinology, vol. 131, No. 4, pp. 2027–2029, Oct. 1992.
European Search Report.
Grompe et al., Genomics 12:755–760 (1992).
Anson et al., Biochem. J. 294:657–662 (1993).
Daniele et al., Genomics 16:755–757 (1993).
Yen et al., Cell 49:443–454 (1987).

*Primary Examiner*—Charles L. Patterson, Jr.
*Assistant Examiner*—T. MacAllister
*Attorney, Agent, or Firm*—Finnegan, Henderson, Farabow, Garrett & Dunner, L.L.P.

[57] ABSTRACT

A bone-related protein named OSF-8 which is obtained from bone tissue of a mammal including mouse or human, and a process for its production. This protein is a novel naturally occurring mammal protein which belongs to a group of sulfatases. OSF-8 degrades the sulfate groups of the sugar chains of proteoglycan, which makes up the cartilage matrix, during the replacement of cartilage into bone tissue at the stage of osteogenesis. OSF-8 can be used as an agent for treating bone metabolic diseases, and its high organ specificity for bones enables its use as a diagnostic reagent for bone metabolic diseases.

3 Claims, 1 Drawing Sheet

BONE-RELATED SULFATASE-LIKE PROTEIN AND PROCESS FOR ITS PRODUCTION

This application is a continuation of application Ser. No. 08/111,887, filed Aug. 26, 1993, now abandoned.

The present invention provides a novel bone-related protein. This invention relates to a novel protein having the abilities to form and maintain bones as well as cartilages (a novel sulfatase, osteocyte specific factor OSF-8); a method for measuring its activity; a method for detecting an inhibitor or enhancer of its activity; DNA coding for the OSF-8 and a process for the production of that protein by a genetic engineering technique using the DNA; and applications of specific antibodies, comprising the purified protein, the genetically engineered protein, or a partial peptide thereof, to immunoassay for diagnosis of metabolic bone diseases.

Bone metabolic diseases include osteoporosis, Paget's disease, osteomalacia, hyperostosis, and osteopetrosis. Osteoporosis, in particular, has a high incidence enough to affect about more than a half of postmenopausal women and elderly people, and effective methods for its diagnosis and treatment have been strongly desired.

Bone metabolic diseases involve some disorder of bone metabolism at the cellular level in bone tissue. The discovery, isolation and identification of factors associated specifically with bone metabolism are very effective for elucidating this disorder.

A cell line of an osteoblast, which plays a major role in osteogenesis, was used to identify a proteinaceous factor produced specifically by this cell line. Therefore, the present invention provides a novel protein named OSF-8 which is substantially bone-specific, and which has a high homology with various known sulfatases in terms of amino acid sequence.

OSF-8 can also be produced from the DNA sequence described in the present specification by an ordinary genetic engineering technique known in the art.

Furthermore, the OSF-8 or its fragment can be produced from the amino acid sequence described in the specification by a chemical peptide synthesis method. Moreover, that fragment of the DNA sequence of the OSF-8 described in the present invention which has a high specificity particularly for other sulfatases can be synthesized with a length of 15 to 50 bases by an ordinary chemical oligonucleotide synthesis method. That fragmentary sequence can be used as a DNA probe for finding and identifying bone-derived cells. This identification of bone-derived cells is useful particularly for grasping the origin of metastatic or recurrent carcinoma, thus leading to an appropriate therapy for recurrent cancer. Of the partial peptides of the OSF-8, the peptide in the epitope portion that can be recognized by antibodies is usable for preparing a monoclonal antibody specific for OSF-8. The resulting monoclonal antibody is of marked value for identifying bone-derived cells by an immunological cell tissue staining method.

The following is known about the relationship between bone metabolism and the enzymes in a group of sulfatases where the OSF-8 belongs.

Histological observations have shown that cartilages are first formed during osteogenesis of long bones and in the fractured bone repairing process. In the process of calcification of the cartilages, angiogenesis is observed and migrated cells such as osteoblasts and osteoclasts can change the cartilages into bone tissue, although details of the mechanisms at the protein level are unknown. In addition to the presence of calcium phosphate deposition in bone, a marked difference in the constitution of the matrix protein is known between the bone and the cartilage. More than 50% of the dry weight of the cartilage is large proteoglycan, and the collagen involved is type II. Whereas more than 90% of the bone is type I collagen; large proteoglycan in the cartilage disappears at cartilage ossification, and only small proteoglycan and non-collagenous proteins are present. Thus, marked replacement of the matrix is inevitable during the process of cartilage ossification. Migrated cells, most likely, osteoblasts and osteoclasts, may play a central role in the digestion of the cartilage as well as the construction of the osteoid. These osteoblasts have been shown to differentiate from mesenchymal cells, suggesting that they may migrate, attendant on angiogenesis, into the tissue prior to the ossification of the mesochondrium. The absorption of the cartilage requires not only the presence of collagenase which digests type II collagen accounting for about 50% of the cartilage matrix proteins, but also the digestion of sugar chains having sulfate groups present widely in the cartilage (e.g. chondroitin sulfate, keratan sulfate). To date, however, there have been no reports of sulfuric ester hydrolases (sulfatases) inherent in cartilage and bone tissue.

On the other hand, the involvement of estrogen in bone metabolism is well known. Osteoporosis occurs in many postmenopausal women, and the administration of estrogen to these patients can inhibit the loss of bone mineral volume. However, the concrete mechanism of action of estrogen in bone tissue is unclear. Estrogen is biosynthesized in breast cancer cells that are highly sensitive to it. Aromatase which takes part in the conversion of androgen into estrogen, and sulfatase which synthesizes estrogen from estrone sulfate are attracting attention as estrogen synthesizing enzymes. In recent years, osteoblasts have been reported to have aromatase activity. It is highly conceivable that the sulfatase described in the present specification may contribute to estrogen synthesis in osteoblasts. During the period of normal gonadal function, such estrogen synthesis in osteoblasts is physiologically unimportant. After menopause, hormone synthesis in peripheral tissues such as osteoblasts may become important, because a sufficient supply of estrogen is not obtained from the gonads. Such a difference in the ability to synthesize estrogen in osteoblasts may explain the fact that not all postmenopausal women show a sharp decrease in bone mineral volume. Thus, the activation of this estrogen synthesis in osteoblasts may prevent postmenopausal osteoporosis. Furthermore, the postmenopausal assay of sulfatase activity against estrone sulfate in osteoblasts may detect a high risk group for osteoporosis at an early stage. However, such sulfatase has not been reported with osteoblasts.

Therefore, the object of the present invention is to find a new type of protein with sulfatase activity which is expressed specifically in osteoblasts. Such a protein degrades the sulfate groups of the sugar chains of proteoglycan, which makes up the cartilage matrix, during the replacement of cartilage into bone tissue at the stage of osteogenesis. Said protein is also expected to increase local production of estrogen, particularly, in matured bone tissue, when gonadal function has declined.

cDNA of mouse OSF-8 (mOSF-8) was isolated from mouse osteoblastic cell line MC3T3-E1 cDNA library constructed by a combination of PCR (polymerase chain reaction) and the subtraction method, and by the differential screening method. Search through the currently available DNA and amino acid sequence data bases showed the cDNA sequence described in the present invention to be novel. The OSF-8 encoding DNAs of other animals can be obtained from cDNA libraries or genomic libraries constructed from their bones, cultured osteoblasts and other body tissues, by recombinant gene technology using the cDNA or its DNA fragment as a probe.

OSF-8, moreover, is a sulfatase molecule which has homology with known representative sulfatase molecules, but which belongs to a new subclass different from those so far reported.

That is, the protein indicated in the present specification is an osteoblast-specific sulfatase indispensable for normal osteogenesis. Many diseases involving sulfatase deficiency or mutation are widely known to induce the deformation or functional deterioration of the tissue, because the sulfate group-bearing sugar chains in the tissue cannot be digested, thereby causing accumulation of the undigested matter in the cells. It can be easily speculated that the deficiency and functional disorder of this protein may be one of the causes of congenital diseases such as osteogenesis imperfecta.

These congenital diseases can be diagnosed by observing the abnormality of the DNA sequence of this protein. The function of osteoblasts can also be known by measuring the activity or concentration of this protein that has been liberated into body fluids. These facts show that the activity and concentration of this protein can be used as markers of bone metabolism. The addition of this protein to cartilage or the bone matrix may also promote osteogenesis. Many bone and cartilage matrix proteins are known to participate in osteogenesis. Of them, growth factors such as TGF-β are considered to be bound to the proteoglycan of the matrices and accumulated there. The addition of sulfatase could promote the release of these growth factors from the matrices. In states involving the excessive resorption of cartilage, such as rheumatoid arthritis or osteoarthritis, the inhibitor of this protein could be an effective therapeutic agent.

Generally, the OSF-8 can be directly extracted from bone tissue or cartilage tissue of a human, bovine, murine or other source by a known biochemical technique.

The DNA coding for the OSF-8 can be obtained by constructing a cDNA library or a genomic library from mRNA extracted from vertebrate bone tissue, and using a probe comprising a labeled fragment of the mouse DNA sequence disclosed in the present specification. A full length cDNA clone can be obtained by a combination of the above-described and other standard techniques on molecular biology.

The present invention further provides polypeptides comprising analogues of OSF-8, i.e. mutants and fused proteins, as well as fragments of the OSF-8. This invention also provides a process for producing the OSF-8 by recombinant DNA technology.

According to the present application the term "hybridization under stringent conditions means hybridization conditions" with a salt concentration of 6×SSC (NaCl-citrate puffer) at 62°–68° C.

BRIEF EXPLANATION OF FIGURES

Table 1 shows an alignment of the amino acid sequences of mouse OSF-8 and other salfatase molecules. Common amino acid residues are shown in the form of a consensus.

Table 2 shows a continuation of the alignment of the amino acid sequences of mouse OSF-8 and other sulfatase molecules shown in Table 1. Common amino acid residues are shown in the form of a consensus.

Table 3 shows a continuation of the alignment of the amino acid sequences of mouse OSF-8 and other sulfatase molecules shown in Table 2. Common amino acid residues are shown in the form of a consensus.

It is mentioned that the contents of the Japanese priority applications No. 230030/92 and 324034/92 are a part of the present application.

EXAMPLES

The present invention will be described in more detail by reference to the following Examples:

Example 1

Construction of cDNA Library by Subtraction and PCR

The construction of a cDNA library specific for the osteoblastic cell line MC3T3-E1 will be hereinafter described. This cDNA library is constructed by a combination of the subtraction method and the PCR with the gene expressed in mouse liver tissue being subtracted. Each cDNA clone has gene fragments with an average length of about 300 bases, and is characterized in that the gene with a low content has been amplified.

Unless otherwise specified, all general recombinant DNA protocols complied with Sambrook et al., "Molecular Cloning Manual" (1989), Cold Spring Harbor Laboratory, Cold Spring Harbor, U.S.A. Total RNAs were extracted from $8 \times 10^7$ MC3T3-E1 cells and about 1 g of mouse liver tissue by the guanidine method. Poly $A^+$RNAs were purified from the total RNAs by means of the commercially available product "Oligo dT Latex mRNA Purification Kit" (Takara Shuzo). cDNAs were synthesized by a cDNA synthesis kit (Amersham) using 1 μg of each poly $A^+$RNA as a template. However, a random primer was used, instead of an oligo dT primer, in an amount of 1.5 times its ordinary amount used, whereby the cDNA chain elongation was restricted to an average length of about 300 bases. After the cDNAs were made double-stranded and blunt-ended by use of the above kit, they were joined with T4 DNA ligase (Takara Shuzo) to the following two DNA linkers, i.e. ATOS-1/2 (SEQ ID NO. 3 and SEQ ID NO: 4) for the MC3T3-E1 cDNA, and ATOS-4/5 (SEQ ID NO: 5 and SEQ ID NO: 6) for the liver cDNA:

ATOS-½:

ATOS-1 5'- CTCTTGCTTGAATTCGGACTA-3'
(SEQ ID NO: 3)
ATOS-2 3'-ACACGAGAACGAACTTAAGCCTGAT-5'
(SEQ ID NO: 4)
ATOS-⅘:

ATOS-4 5'- CTCTTGCTTAAGCTTGGACTA-3'
(SEQ ID NO: 5)
ATOS-5 3'-ACACGAGAACGAATTCGAACCTGAT-5'
(SEQ ID NO: 6)

Then, each reaction product was subjected to DNA amplification by the PCR (polymerase chain reaction) method using ATOS-1 and ATOS-4, respectively, as primers. The amplified DNA concentration was determined with the DNA assay kit "DNA Dipstick" (Invitrogen). The subtraction method was performed using photobiotin (Pirce). Photobiotin (20 ng) was added to 20 μg of the PCR-amplified liver cDNA, and light from a sunlamp 10 cm apart was projected onto the liver cDNA for 10 minutes to label it with biotin.

To 3.0 µg of the labeled liver cDNA was added 0.3 µg of unlabeled MC3T3-E1 cDNA for hybridization. Then, streptavidin (Takara Shuzo) was reacted, and the reaction mixture was extracted with phenol to remove cDNA common to the liver cDNA from the MC3T3-E1 cDNA. The subtraction method was repeated to remove as much of the common cDNA as possible from the MC3T3-E1 cDNA. DNA was amplified by PCR using the aforementioned ATOS-1, and the DNA concentration was measured. This cDNA (10 ng) was digested with the restriction enzyme EcoRI, and then ligated with T4 ligase to 1 µg of the phage vector lambda gt10 (lambda gt10/EcoRI cloning kit, Stratagene) which was digested with EcoRI and dephosphorylated at its ends. The resulting recombinant DNA was packaged into lambda phage particles by use of the in vitro packaging kit "Gigapack-gold" (Stratagene). The recombinant phages were infected into $E.\ coli$ C600 (preserved as HT003 at Japanese Cancer Research Resources Bank, National Institute of Health of Japan), and the organisms were applied to an agar medium along with a soft agar medium to form phage plaques. The efficiency of infection was determined to be $3 \times 10^6$ phage plaques/µg vector DNA.

The resulting cDNA library was subjected to differential screening to select clones with a high specificity for MC3T3-E1. Specifically, $2.25 \times 10^4$ phages were applied to total 10 plates, and the resulting plaques on each plate were transferred to two nylon membrane filters (total 20 filters). These series of plaques were subjected to plaque hybridization using as the probe radiolabeled MC3T3-E1 cDNA for one of the series, and radiolabeled liver cDNA for the other series. In 273 clones, expression was observed with the MC3T3-E1 cDNA probe, but not with the liver cDNA probe. These clones were used as a mini-library in subsequent experiments.

Example 2

Isolation of Mouse OSF-8 Clone

A description will be made of methods to identify a cDNA fragment of OSF-8 as an MC3T3-E1 specific clone from the mini-library constructed in Example 1, and to clone full length cDNA from the cDNA library of MC3T3-E1 with the use of this fragment.

The total RNAs from MC3T3-E1 and liver prepared in Example 1 were spotted in an amount of 1 µg each onto nylon membrane filters. 273 of the filters were prepared, and used for hybridization to be described later on. Separately, the DNA of the inserts of the 273 phage clones prepared in Example 1 was amplified by PCR. This DNA was agarose gel electrophoresed, and main bands were cut out, purified, and radiolabeled for use as a probe. A clone showing expression with MC3T3-E1 cDNA but no expression with liver cDNA upon autoradiography was recloned into a plasmid vector. Specifically, the DNA of the inserts amplified by PCR and then purified was digested with the restriction enzyme EcoRI, and recloned into the EcoRI site of the plasmid vector pUC118 (Takara Shuzo). The DNA sequence of the resulting clone was determined with commercially available "DNA Sequence Kit" (Takara Shuzo) using a universal primer. Search through DNA and protein data bases showed that DNA sequence to constitute a clone homologous with the existing sulfatase. This clone was designated as pMCLS63, and used for subsequent cloning of the full length cDNA.

For cloning of the full length cDNA, blunt-ended double-stranded cDNA was synthesized with the cDNA synthesis kit "cDNA Synthesis System Plus" (Amersham) using 5 µg of the poly $A^+$RNA of MC3T3-E1 purified in Example 1. The resulting cDNA was ligated to EcoRI/NotI adaptor (Takara Shuzo) using T4 ligase, and the product was agarose gel electrophoresed to purify a fragment more than about 700 base pair long. This fragment was joined to the EcoRI site of lambda gt10 phage vector (Stratagene), and packaged into phage particles in the same way as in Example 1. The packages were infected into $E.\ coli$ as in Example 1, and the efficiency of infection was determined to be $1.5 \times 10^7$ phage plaques/µg vector DNA. The aforementioned pMCLS63 was radiolabeled for use as a probe, and $1.0 \times 10^6$ phage clones of the cDNA library were screened by plaque hybridization. Eight positive hybridization signals were obtained, whereafter the NotI fragment of the phage clone with the longest insert was recloned into the NotI site of the plasmid vector pGEM11Zf(+) (Stratagene). The resulting clone was designated as pKOT162.

Example 3

DNA Sequence of Mouse OSF-8

Figure 1:
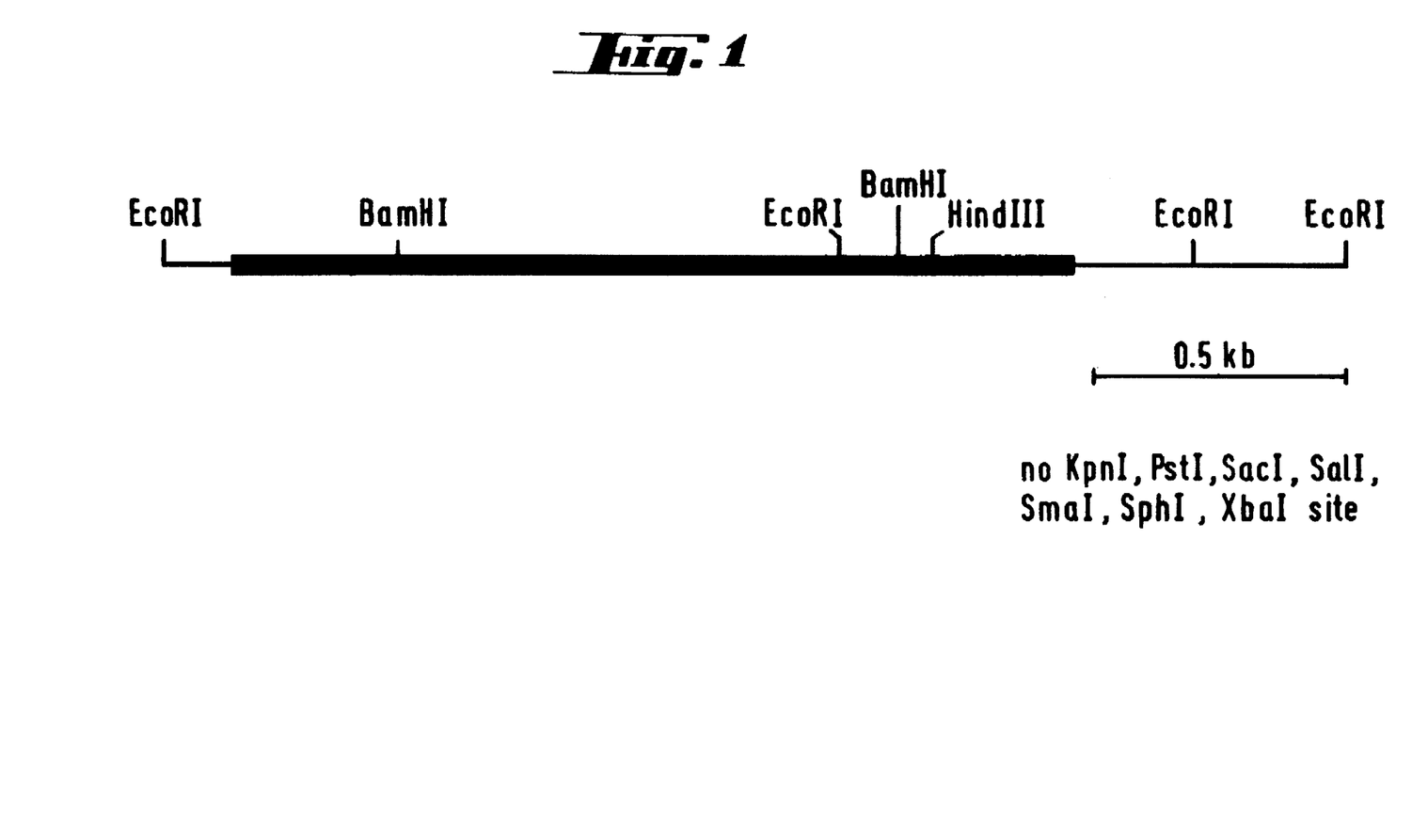
FIG. 1 shows a restriction enzyme map of cDNA coding for mouse OSF-8. The bold letters indicate the region coding for the amino acid of OSF-8. There are no KpnI, PstI, SacI, SalI, SmaI, SphI and XbaI sites.

Deletion mutants of the pKOT162 and a subclone containing its cDNA fragment were prepared with "the Deletion Kit for Kilo Sequence" (Takara Shuzo) by cutting at intervals of 300 base pairs in each opposite direction. The DNA sequence of each deletion mutant was determined with the automatic DNA sequencer 373A (Applied Biosystems, U.S.A.). The entire DNA sequence of the cDNA, and an amino acid sequence translated from this DNA sequence are shown as Sequence ID No. 1 of the Sequence Table. The protein encoded by this cDNA was designated as OSF-8. No. 1 of the amino acid residue corresponds to the N-terminus of the predicted OSF-8 precursor protein. The restriction enzyme map of that cDNA is shown in FIG. 1, and the homology in the amino acid sequence between the mouse OSF-8 and other sulfatases is shown in Tables 1 to 3.

Example 4

Tissue Specific Expression of Mouse OSF-8

RNA dot blotting was performed to investigate the tissue specific expression of mouse OSF-8. The total RNAs of the thymus, spleen, brain, kidney, liver, lung, testis and heart of mice (purchased from Nippon Clea) were prepared by the guanidine method. Calvarial osteoblast-rich cells were obtained from a culture of newborn mice calvaria. Total RNA was extracted from these cells in the same way as described above. One µg of the total RNA each from the above-mentioned tissues, cultured calvarial cells, and MC3T3-E1 was dotted onto nylon membrane filters (Biodyne, PALL), fixed by heating, and used for hybridization. Separately, the pKOT162 was digested with NotI, and purified by agarose gel electrophoresis. Then, the isolate was radiolabeled and used as a probe. Autoradiography indicated high expression for the cultured calvarial cells and MC3T3-E1.

OSF-8 provided by the present invention can be used as an agent for treating bone metabolic diseases, and because of its high organ specificity for bones, it can also be used as a diagnostic reagent for bone metabolic diseases.

TABLE 1

| | 1 | | | | | 50 |
|---|---|---|---|---|---|---|
| mouse OSF-8 | . . . . . . . . . . | . . . . . MP AML | LLLVSVVAAL | ALAAPAPRTQ | KKRMQVNQAP | |
| human aryl-sulfatase A | . . . . . . . . . . | . . . . . . . . . M | SMGAPRSLLL | ALAA. GLAV. | . AR . . . . . PP | |
| human steroid sulfatase | . . . . . . . . . . | . . . . . . MPLR | KMKIPFLLLF | FLWEAESHE. | ASR . . . . . . P | |
| human aryl-sulfatase B | MGPRGAASLP | RGPGPRRLLL | PVVLPLLLLL | LLAPPGSGAG | ASR . . . . . PP | |
| Consensus | ---------- | ---------- | ---------- | -L-------- | --R------P | |
| | 51 | | | | | 100 |
| mouse OSF-8 | NVVLVASDSF | D. GRLTFQPG | SQVVKLPFIN | FMRAHGTTFL | NAYTNSPICC | |
| human aryl-sulfatase A | NIVLIFADDL | GYGDLGCY. G | HPSSTTPNLD | QLAAGGLRFT | DFYVPVSLCT | |
| human steroid sulfatase | NIILVMADDL | GIGDPGCY. G | NKTIRTPNID | RLASGGVKLT | QHLAASPLCT | |
| human aryl-sulfatase B | HLVFLLADDL | GWNDVGFH. G | SR. IRTPHLD | ALAAGGVLLD | NYYTQ. PLCT | |
| Consensus | -------D-- | ---------G | ------P--- | -----G---- | ---------C- | |
| | 101 | | | | | 150 |
| mouse OSF-8 | PSRAAMWSGL | FTHLTESWN. | . . . . . . . . . . | NFKGLDPNYT | TWMDIMEKHG | |
| human aryl-sulfatase A | PSRAALLTGR | LPVRMGMYP. | . . . GVLV. PS | SRGGLPLEEV | TVAEVLAARG | |
| human steroid sulfatase | PSRAAFMTGR | YPVRSGMASW | SRTGVFLFTA | SSGGLPTDEI | TFAKLLKDQG | |
| human aryl-sulfatase B | PSRSQLLTGR | YQIRTGLQH. | . . . . QIIWPC | QPSCVPLDEK | LLPQLLKEAG | |
| Consensus | PSR-----G- | ---------- | ---------- | ---------- | ---------G | |
| | 151 | | | | | 200 |
| mouse OSF-8 | YQTQKFGKVD | YTSGHHS . . . | . . ISNRVEAW | TRDVAFLL . . | . . . . . RQEG. | |
| human aryl-sulfatase A | YLTGMAGKWH | LGVGPEG . . . | . AFLPPHQGF | HRFLGIP . . . | . . . YSHDQGP | |
| human steroid sulfatase | YSTALIGKWH | LGMSCHSKTD | FCHHPLHHGF | NYFYGISLTH | LRDCKPGEGS | |
| human aryl-sulfatase B | YTTHMVGKWH | LGMYRKE . . . | . . CLPTRRGF | DTYPFGYLLGS | EDYYSHERCT | |
| Consensus | Y-T---GK-- | ---------- | ---------- | ---------- | ---------- | |
| | 201 | | | | | 250 |
| mouse OSF-8 | . . . . . RPII | NLIPDKNRRR | VMTKDWQNTD | KAIEWLR. QV | NYTKPFVLYL | |
| human aryl-sulfatase A | C . . . . QNLT | CFPP . . . . . . | . ATPCDGGCD | QGLVPIPL . . | . . . . . . LANL | |
| human steroid sulfatase | VFTTGFKRLV | FLPLQIVGVT | LLTLAALNC. | LGLLHVPLGV | FFSLLFLAAL | |
| human aryl sulfatase B | . . . . . . . . LI | DALN . . . . . . | . VTRCALDFR | DG . . . . . . . . | . . . . . . . . . . | |
| Consensus | ---------- | ---------- | --T------- | ---------- | ---------- | |
| | 251 | | | | | 300 |
| mouse OSF-8 | GLNLPHPYPS | PSSGENF . . . | . . . . . . . GSS | TFHTSLYWLE | KVAYDAI . . . | |
| human aryl-sulfatase A | SVEAQPPWLP | GLEA . . . . . . | . . . . . . . . . . | RYMAFAHDL. | . MADA . . . QR | |
| human steroid sulfatase | ILTLFLGFLH | YFRPLNCFMM | RNYEIIQQPM | SYDNLTQRLT | VEAAQFI. QR | |
| human aryl-sulfatase B | EEVATGYKN | MYS . . . . . . . | . . . . . . . . . . | . . . . . . . . . . | . . . . . TNIFT | KRAIALITNH |
| Consensus | ---------- | ---------- | ---------- | ---------- | --A------- | |

TABLE 2

| | 301 | | | | | 350 |
|---|---|---|---|---|---|---|
| mouse OSF-8 | . . KIPKWLTL | . . SQMH. PVD | FCSSYTKNCT | GKFTENEIKN | IRAFYYAMCA | |
| human aryl-sulfatase A | Q. DRPFFLYY | ASHHTHYPQ. | FSGQ . . . . . . | . SFAE . . . RS | GRGPFGDSLM | |
| human steroid sulfatase | NTETPFLLVL | SYLHVHTAL. | FSSK . . . . . . | . DFAG . . . KS | QHGVYGDAVE | |
| human aryl-sulfatase B | PPEKPLFLYL | ALQSVHEPLQ | VPEEYLKPY. | . DFIQ . . . DK | NRHHYAGMVS | |
| Consensus | ----P--L-- | -----H---- | ---------- | --F------- | ---------- | |
| | 351 | | | | | 400 |
| mouse OSF-8 | ETDAMLGEII | LALHKLDLLQ | KTIVIYTSDH | GEMAMEHRQF | Y . . . . . . . . . | |
| human aryl-sulfatase A | ELDAAVGTLM | TAIGDLGLLE | ETLVIFTADN | GPETMRMS . . | . . . RGGCSGL | |
| human steroid sulfatase | EMDWSVGQIL | NLLDELRLAN | DTLIYFTSDQ | GAHVEEVSSK | GEIHGGSNGI | |
| human aryl-sulfatase B | LMDEAVGNVT | AALKSSGLWN | NTVFIFSTDN | GGQTLA . . . . | . . . . GGNNWP | |
| Consensus | --D---G--- | -------L-- | -T------D- | G--------- | ---------- | |
| | 401 | | | | | 450 |

TABLE 2-continued

| | | | | | |
|---|---|---|---|---|---|
| mouse OSF-8 | .... KMSMYE | ASVHVPLLMM | GPG.IKANLQ | VPSVVSLVDI | YPTMLDIAGI |
| human aryl-sulfatase A | LRCGKGTTYE | GGVREPALAF | WPGHIAPGV. | THELASSLDL | LPTLAALAGA |
| human steroid sulfatase | YKGGKANNWE | GGIRVPGILR | WPRVIQAGQK | IDEPTSNMDI | FPTVAKLAGA |
| human aryl-sulfatase B | LRGRKWSLWE | GGVRGVGFVA | SPLLKQKGVK | NRELIHISDW | LPTLVKLARG |
| Consensus | ----K----E | ---------- | -P-------- | --------D- | -PT----A-- |
| | | | | | 500 |
| mouse OSF-8 | ALPPN..LSG | YSLLTLLSNA | SAN.EQAFKF | HRPPWIL... | .......... |
| human aryl-sulfatase A | PLP.NVTLDG | FDLSPLLLGT | GKSPRQS.LF | FYPS.YPD.. | .......... |
| human steroid sulfatase | PLPEDRIIDG | RDLMPLLEGK | SQRSDHEFLF | HYCNAYLN.. | .......... |
| human aryl-sulfatase B | HTNGTKPLDG | FDMWKTISEG | SPSPRIELLH | NIDPNFVDSS | PCPRNSMAPA |
| Consensus | --------G- | ---------- | ---------- | ---------- | ---------- |
| | 501 | | | | 550 |
| mouse OSF-8 | ...SEFHGCN | A.NASTYMLR | ..T..GQW.K | YIAYADGAS. | ......VQPQ |
| human aryl-sulfatase A | ....EVRGVF | AVRTGKYKAH | FFT..QGSAH | SDTTADPACH | AS....SSLT |
| human steroid sulfatase | ....AVRWHP | QNSTSIWKAF | FFT...PNFNP | VGSNGCFATH | VCFCFGSYVT |
| human aryl-sulfatase B | KDDSSLPEYS | AFNTSVHAAI | RHGNWKLLTG | YPGCGYWFPP | PSQYNVSEIP |
| Consensus | ---------- | ---------- | ---------- | ---------- | ---------- |
| | | | | | 600 |
| mouse OSF-8 | .......... | LFDLSLDPDE | LTNIATEFPE | ITYSLDQKLR | SIVNYPKVSA |
| human aryl-sulfatase A | AHEPP....L | LYDLSKDPGE | NYNLLGGVAG | ATPEVLQALK | QL........ |
| human steroid sulfatase | HHDPP....L | LFDISKDPRE | RNPL...TPA | SEPRFYEILK | VM........ |
| human aryl-sulfatase B | SSDPPTKTLW | LFDIDRDPEE | RHDLSTEYPH | IVTKLLSRL. | .......... |
| Consensus | ---------- | L-D---DP-E | ---------- | --------L- | ---------- |

TABLE 3

| | 601 | | | | 650 |
|---|---|---|---|---|---|
| mouse OSF-8 | SVHQYNKEQF | IMWKQSVGQN | YSNVIAHLRW | HQDWQRDPRK | YENAIQHWLT |
| human aryl-sulfatase A | ...QLLKAQL | ...DAAVT.F | GPSQVARGE. | ......DP.. | ........ALQ |
| human steroid sulfatase | ...QEAADRH | ...TQTLP.E | VPDQFSWNN. | ...FLWKP.. | ........WLQ |
| human aryl-sulfatase B | ...QFY...H | ...KHSVPVY | FPAQDPRCDP | KATGVWGP.. | ........WM. |
| Consensus | ---Q------ | ---------- | ---------- | -------P-- | ---------- |

| | | | | 677 | |
|---|---|---|---|---|---|
| mouse OSF-8 | AHSSPLASSP | TQSTSGSQPT | LPQSTSG | | (SEQ. ID. NO: 7) |
| human aryl-sulfatase A | ICCHPGCTPR | PACCHCPDPH | A...... | | (SEQ. ID. NO: 8) |
| human steroid sulfatase | LCCPST.... | GLSCQCDREK | QDKRLSR | | (SEQ. ID. NO: 9) |
| human aryl-sulfatase B | .......... | .......... | ....... | | (SEQ. ID. NO: 10) |
| Consensus | ---------- | ---------- | ------- | | (SEQ. ID. NO: 11) |

What is claimed is:

1. A process for the production of a recombinant mammalian osteocyte specific factor OSF-8 protein comprising the steps of:

(a) obtaining a population of cells containing a heterologous DNA composed of the following DNA sequences:
   (i) a sequence that can function in the cells to control transcription and translation, and
   (ii) a DNA sequence joined downstream of said controlling sequence to code for said recombinant OSF-8 protein, and
(b) culturing said population of cells under conditions which permit the production of said recombinant protein; and wherein said OSF-8 protein comprises mouse OSF-8 having an amino acid sequence at the 19th to 556th positions in Sequence ID No. 2 of the Sequence Listing.

2. The process of claim 1 wherein the controlling sequence further contains a DNA coding for a signal peptide for secreting said recombinant protein extracellularly such that said DNA is positioned immediately upstream of said DNA sequence coding for said recombinant protein.

3. The process of claim 1 wherein the population of cells is *Escherichia coli*, or yeast, or mammalian cells.

* * * * *

UNITED STATES PATENT AND TRADEMARK OFFICE
CERTIFICATE OF CORRECTION

PATENT NO. : 5,627,050  
DATED : May 06, 1997  
INVENTOR(S) : Sunao TAKESHITA et al.

It is certified that error appears in the above-indentified patent and that said Letters Patent is hereby corrected as shown below:

Title page, In the Related U.S. Application Data, item [63], the date "May 26, 1993" should read --August 26, 1993--.

Signed and Sealed this

Twelfth Day of August, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 2373 base pairs
( B ) TYPE: nucleic acid -continued ( C ) STRANDEDNESS: double
( D ) TOPOLOGY: linear ( i i ) MOLECULE TYPE: cDNA to mRNA ( v i ) ORIGINAL SOURCE:
    ( A ) ORGANISM: Mus musculus
    ( B ) STRAIN: Osteoblastic cell line MC3T3E1

( i x ) FEATURE:
    ( A ) NAME/KEY: CDS
    ( B ) LOCATION: 150..1817

( x i ) SEQUENCE DESCRIPTION: SEQ ID NO:1:

```
GAATTCGCGG CCGCAGTTTC TAGGTGCCGC TCATATTTAC TTCTGTATTT GTAAGCCAAA        60

CTTCTAGTCT TGTCCCTAGA GTCCGGCCCC TGCTCATGAC TGGAGAGCAG GCTACAGGAG       120

CCCCGCTCAG CAGCCGCTTC TGAACGGCC ATG CCC GCG ATG CTG TTG CTG TTG        173
                                 Met Pro Ala Met Leu Leu Leu Leu
                                  1                   5

GTG TCG GTG GTC GCA GCG TTA GCA CTC GCA GCA CCG GCC CCC AGA ACA        221
Val Ser Val Val Ala Ala Leu Ala Leu Ala Ala Pro Ala Pro Arg Thr
         10                  15                  20

CAG AAG AAA AGG ATG CAA GTG AAC CAG GCG CCC AAC GTG GTG CTG GTC        269
Gln Lys Lys Arg Met Gln Val Asn Gln Ala Pro Asn Val Val Leu Val
 25                  30                  35                  40

GCC AGT GAC TCC TTC GAT GGA AGA CTA ACA TTT CAA CCA GGA AGT CAG        317
Ala Ser Asp Ser Phe Asp Gly Arg Leu Thr Phe Gln Pro Gly Ser Gln
                     45                  50                  55

GTA GTA AAA CTT CCC TTC ATT AAC TTC ATG AGA GCA CAT GGC ACC ACC        365
Val Val Lys Leu Pro Phe Ile Asn Phe Met Arg Ala His Gly Thr Thr
                 60                  65                  70

TTC CTA AAT GCC TAC ACT AAT TCA CCC ATC TGC TGT CCA TCA CGT GCA        413
Phe Leu Asn Ala Tyr Thr Asn Ser Pro Ile Cys Cys Pro Ser Arg Ala
             75                  80                  85

GCA ATG TGG AGT GGC CTC TTC ACT CAC TTG ACA GAA TCT TGG AAT AAT        461
Ala Met Trp Ser Gly Leu Phe Thr His Leu Thr Glu Ser Trp Asn Asn
         90                  95                 100

TTT AAG GGT CTG GAT CCA AAT TAT ACG ACA TGG ATG GAC ATC ATG GAG        509
Phe Lys Gly Leu Asp Pro Asn Tyr Thr Thr Trp Met Asp Ile Met Glu
105                 110                 115                 120

AAG CAT GGC TAT CAG ACA CAG AAA TTT GGA AAA GTG GAC TAT ACT TCA        557
Lys His Gly Tyr Gln Thr Gln Lys Phe Gly Lys Val Asp Tyr Thr Ser
                125                 130                 135

GGA CAT CAT TCC ATT AGT AAC CGT GTG GAA GCA TGG ACA AGA GAT GTT        605
Gly His His Ser Ile Ser Asn Arg Val Glu Ala Trp Thr Arg Asp Val
            140                 145                 150

GCA TTC TTG CTC CGA CAA GAA GGC AGA CCC ATA ATT AAT CTT ATC CCT        653
Ala Phe Leu Leu Arg Gln Glu Gly Arg Pro Ile Ile Asn Leu Ile Pro
        155                 160                 165

GAT AAG AAT AGA AGG AGA GTG ATG ACC AAG GAC TGG CAG AAT ACA GAC        701
Asp Lys Asn Arg Arg Arg Val Met Thr Lys Asp Trp Gln Asn Thr Asp
170                 175                 180

AAA GCA ATC GAA TGG CTA AGA CAG GTT AAC TAC ACC AAG CCA TTT GTC        749
Lys Ala Ile Glu Trp Leu Arg Gln Val Asn Tyr Thr Lys Pro Phe Val
185                 190                 195                 200

CTT TAC TTG GGA TTG AAT TTG CCA CAC CCT TAC CCT TCA CCA TCT TCA        797
Leu Tyr Leu Gly Leu Asn Leu Pro His Pro Tyr Pro Ser Pro Ser Ser
                205                 210                 215

GGA GAA AAC TTT GGC TCT TCT ACG TTT CAC ACT TCC CTT TAC TGG CTT        845
Gly Glu Asn Phe Gly Ser Ser Thr Phe His Thr Ser Leu Tyr Trp Leu
            220                 225                 230

GAA AAG GTA GCT TAT GAT GCA ATC AAA ATC CCA AAG TGG CTG ACT TTG        893
```

-continued

| | | | | | | | | | | | | | | | |
|---|---|---|---|---|---|---|---|---|---|---|---|---|---|---|---|
| Glu | Lys | Val | Ala | Tyr | Asp | Ala | Ile | Lys | Ile | Pro | Lys | Trp | Leu | Thr | Leu |
| | | 235 | | | | | 240 | | | | | 245 | | | |

| TCA | CAA | ATG | CAC | CCT | GTG | GAT | TTT | TGC | TCC | TCC | TAT | ACA | AAA | AAC | TGC | 941 |
|---|---|---|---|---|---|---|---|---|---|---|---|---|---|---|---|---|
| Ser | Gln | Met | His | Pro | Val | Asp | Phe | Cys | Ser | Ser | Tyr | Thr | Lys | Asn | Cys | |
| 250 | | | | | 255 | | | | | 260 | | | | | | |

| ACT | GGG | AAA | TTT | ACT | GAA | AAT | GAA | ATT | AAG | AAC | ATT | AGA | GCA | TTT | TAT | 989 |
|---|---|---|---|---|---|---|---|---|---|---|---|---|---|---|---|---|
| Thr | Gly | Lys | Phe | Thr | Glu | Asn | Glu | Ile | Lys | Asn | Ile | Arg | Ala | Phe | Tyr | |
| 265 | | | | | 270 | | | | | 275 | | | | | 280 | |

| TAT | GCT | ATG | TGT | GCT | GAG | ACA | GAT | GCC | ATG | CTA | GGT | GAA | ATT | ATT | TTG | 1037 |
|---|---|---|---|---|---|---|---|---|---|---|---|---|---|---|---|---|
| Tyr | Ala | Met | Cys | Ala | Glu | Thr | Asp | Ala | Met | Leu | Gly | Glu | Ile | Ile | Leu | |
| | | | | 285 | | | | | 290 | | | | | 295 | | |

| GCT | CTT | CAC | AAG | TTA | GAT | CTT | CTT | CAG | AAA | ACT | ATT | GTT | ATA | TAT | ACC | 1085 |
|---|---|---|---|---|---|---|---|---|---|---|---|---|---|---|---|---|
| Ala | Leu | His | Lys | Leu | Asp | Leu | Leu | Gln | Lys | Thr | Ile | Val | Ile | Tyr | Thr | |
| | | | 300 | | | | | 305 | | | | | 310 | | | |

| TCA | GAC | CAT | GGA | GAG | ATG | GCT | ATG | GAA | CAC | CGC | CAG | TTT | TAT | AAA | ATG | 1133 |
|---|---|---|---|---|---|---|---|---|---|---|---|---|---|---|---|---|
| Ser | Asp | His | Gly | Glu | Met | Ala | Met | Glu | His | Arg | Gln | Phe | Tyr | Lys | Met | |
| | | | 315 | | | | | 320 | | | | | 325 | | | |

| AGT | ATG | TAT | GAA | GCT | AGT | GTC | CAT | GTT | CCT | CTT | CTG | ATG | ATG | GGA | CCA | 1181 |
|---|---|---|---|---|---|---|---|---|---|---|---|---|---|---|---|---|
| Ser | Met | Tyr | Glu | Ala | Ser | Val | His | Val | Pro | Leu | Leu | Met | Met | Gly | Pro | |
| | 330 | | | | | 335 | | | | | 340 | | | | | |

| GGA | ATT | AAG | GCC | AAC | CTA | CAA | GTA | CCA | AGT | GTT | GTT | TCT | CTT | GTG | GAT | 1229 |
|---|---|---|---|---|---|---|---|---|---|---|---|---|---|---|---|---|
| Gly | Ile | Lys | Ala | Asn | Leu | Gln | Val | Pro | Ser | Val | Val | Ser | Leu | Val | Asp | |
| 345 | | | | | 350 | | | | | 355 | | | | | 360 | |

| ATC | TAC | CCT | ACT | ATG | CTT | GAC | ATT | GCT | GGG | ATT | GCT | CTG | CCT | CCA | AAT | 1277 |
|---|---|---|---|---|---|---|---|---|---|---|---|---|---|---|---|---|
| Ile | Tyr | Pro | Thr | Met | Leu | Asp | Ile | Ala | Gly | Ile | Ala | Leu | Pro | Pro | Asn | |
| | | | | 365 | | | | | 370 | | | | | 375 | | |

| CTG | AGT | GGA | TAC | TCC | TTG | TTG | ACG | CTG | TTG | TCA | AAT | GCA | TCT | GCA | AAT | 1325 |
|---|---|---|---|---|---|---|---|---|---|---|---|---|---|---|---|---|
| Leu | Ser | Gly | Tyr | Ser | Leu | Leu | Thr | Leu | Leu | Ser | Asn | Ala | Ser | Ala | Asn | |
| | | | 380 | | | | | 385 | | | | | 390 | | | |

| GAA | CAG | GCA | TTC | AAA | TTC | CAC | CGT | CCA | CCT | TGG | ATT | CTG | AGT | GAA | TTC | 1373 |
|---|---|---|---|---|---|---|---|---|---|---|---|---|---|---|---|---|
| Glu | Gln | Ala | Phe | Lys | Phe | His | Arg | Pro | Pro | Trp | Ile | Leu | Ser | Glu | Phe | |
| | | 395 | | | | | 400 | | | | | 405 | | | | |

| CAT | GGA | TGC | AAT | GCA | AAT | GCT | TCT | ACC | TAC | ATG | CTA | CGA | ACT | GGC | CAG | 1421 |
|---|---|---|---|---|---|---|---|---|---|---|---|---|---|---|---|---|
| His | Gly | Cys | Asn | Ala | Asn | Ala | Ser | Thr | Tyr | Met | Leu | Arg | Thr | Gly | Gln | |
| | 410 | | | | | 415 | | | | | 420 | | | | | |

| TGG | AAG | TAC | ATA | GCC | TAC | GCT | GAT | GGT | GCT | TCC | GTG | CAG | CCT | CAG | CTC | 1469 |
|---|---|---|---|---|---|---|---|---|---|---|---|---|---|---|---|---|
| Trp | Lys | Tyr | Ile | Ala | Tyr | Ala | Asp | Gly | Ala | Ser | Val | Gln | Pro | Gln | Leu | |
| 425 | | | | | 430 | | | | | 435 | | | | | 440 | |

| TTC | GAT | CTT | TCC | TTG | GAT | CCG | GAT | GAG | CTA | ACA | AAC | ATT | GCT | ACA | GAA | 1517 |
|---|---|---|---|---|---|---|---|---|---|---|---|---|---|---|---|---|
| Phe | Asp | Leu | Ser | Leu | Asp | Pro | Asp | Glu | Leu | Thr | Asn | Ile | Ala | Thr | Glu | |
| | | | | 445 | | | | | 450 | | | | | 455 | | |

| TTT | CCA | GAA | ATT | ACT | TAT | TCT | TTG | GAC | CAG | AAG | CTT | CGT | TCT | ATT | GTA | 1565 |
|---|---|---|---|---|---|---|---|---|---|---|---|---|---|---|---|---|
| Phe | Pro | Glu | Ile | Thr | Tyr | Ser | Leu | Asp | Gln | Lys | Leu | Arg | Ser | Ile | Val | |
| | | | 460 | | | | | 465 | | | | | 470 | | | |

| AAC | TAC | CCT | AAA | GTG | TCT | GCT | TCT | GTC | CAT | CAG | TAC | AAT | AAA | GAA | CAG | 1613 |
|---|---|---|---|---|---|---|---|---|---|---|---|---|---|---|---|---|
| Asn | Tyr | Pro | Lys | Val | Ser | Ala | Ser | Val | His | Gln | Tyr | Asn | Lys | Glu | Gln | |
| | | 475 | | | | | 480 | | | | | 485 | | | | |

| TTT | ATC | ATG | TGG | AAG | CAA | AGC | GTA | GGG | CAA | AAT | TAC | TCA | AAC | GTT | ATA | 1661 |
|---|---|---|---|---|---|---|---|---|---|---|---|---|---|---|---|---|
| Phe | Ile | Met | Trp | Lys | Gln | Ser | Val | Gly | Gln | Asn | Tyr | Ser | Asn | Val | Ile | |
| | 490 | | | | | 495 | | | | | 500 | | | | | |

| GCA | CAC | CTC | AGA | TGG | CAT | CAA | GAT | TGG | CAG | AGA | GAT | CCA | AGG | AAG | TAT | 1709 |
|---|---|---|---|---|---|---|---|---|---|---|---|---|---|---|---|---|
| Ala | His | Leu | Arg | Trp | His | Gln | Asp | Trp | Gln | Arg | Asp | Pro | Arg | Lys | Tyr | |
| 505 | | | | | 510 | | | | | 515 | | | | | 520 | |

| GAA | AAT | GCA | ATC | CAA | CAT | TGG | CTC | ACA | GCC | CAC | TCC | AGT | CCA | CTG | GCT | 1757 |
|---|---|---|---|---|---|---|---|---|---|---|---|---|---|---|---|---|
| Glu | Asn | Ala | Ile | Gln | His | Trp | Leu | Thr | Ala | His | Ser | Ser | Pro | Leu | Ala | |
| | | | | 525 | | | | | 530 | | | | | 535 | | |

| AGC | AGC | CCA | ACC | CAG | TCC | ACC | AGT | GGC | TCA | CAG | CCC | ACT | CTT | CCC | CAG | 1805 |
|---|---|---|---|---|---|---|---|---|---|---|---|---|---|---|---|---|
| Ser | Ser | Pro | Thr | Gln | Ser | Thr | Ser | Gly | Ser | Gln | Pro | Thr | Leu | Pro | Gln | |
| | | | 540 | | | | | 545 | | | | | 550 | | | |

| TCC | ACC | AGT | GGC | TAGCAGCCTA | CTCCAGTGAC | CAGTGACTCA | TAGCCCACTC | 1857 |
|---|---|---|---|---|---|---|---|---|
| Ser | Thr | Ser | Gly | | | | | |

-continued

```
Ser  Thr  Ser  Gly
          555
```

| | | | | |
|---|---|---|---|---|
| TTCTCCAGTC | CACCAGTGGT | TAGCATCCCA | CTTCAATCCA | CCAGTAGCTC ACAGCCTACT | 1917 |
| CTTCTCCAGT | AGCAGTAGAC | AATAATAAAA | CTTTCTCAAG | CTATATGTGA ATATGTTGGT | 1977 |
| ACATACTAAA | CTGAATCAGC | CTTAACAATT | ATTAAAATTA | CTTATTTTCA AAATATGTAC | 2037 |
| TATATATTAC | TTGCCAATGA | ATACAGAATT | CATATTTTCA | AAACTAGTTA TACTAAGACC | 2097 |
| TTATTGTTGC | AGACCTCTGA | CAGTTTAACG | TCAGAAGTAT | TTAAAGAATA GAAGCAAGCA | 2157 |
| TTCTTACTGT | TTCCCTGGAT | AATACAGAAT | ATGAAATATT | TAACAACTA TCAGTTGTTA | 2217 |
| TTTATGAATC | ATGATGTCTC | GTGACTGACT | AGTTTTTTGG | TAAAACTCTT TGGAAGTATT | 2277 |
| TGATGTGTTA | GAACTATTA | ATGGGACATA | GACTCTGAAT | ATAGTTGATT TTACTTTCTG | 2337 |
| TTGTTTAAAA | AAAAAAAAA | AAGCGGCCGC | GAATTC | | 2373 |

( 2 ) INFORMATION FOR SEQ ID NO:2:

( i ) SEQUENCE CHARACTERISTICS:
        ( A ) LENGTH: 556 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met  Pro  Ala  Met  Leu  Leu  Leu  Leu  Val  Ser  Val  Val  Ala  Ala  Leu  Ala
 1              5                        10                       15

Leu  Ala  Ala  Pro  Ala  Pro  Arg  Thr  Gln  Lys  Lys  Arg  Met  Gln  Val  Asn
              20                       25                       30

Gln  Ala  Pro  Asn  Val  Val  Leu  Val  Ala  Ser  Asp  Ser  Phe  Asp  Gly  Arg
         35                       40                       45

Leu  Thr  Phe  Gln  Pro  Gly  Ser  Gln  Val  Val  Lys  Leu  Pro  Phe  Ile  Asn
     50                       55                       60

Phe  Met  Arg  Ala  His  Gly  Thr  Thr  Phe  Leu  Asn  Ala  Tyr  Thr  Asn  Ser
 65                       70                       75                       80

Pro  Ile  Cys  Cys  Pro  Ser  Arg  Ala  Ala  Met  Trp  Ser  Gly  Leu  Phe  Thr
                    85                       90                       95

His  Leu  Thr  Glu  Ser  Trp  Asn  Asn  Phe  Lys  Gly  Leu  Asp  Pro  Asn  Tyr
               100                      105                      110

Thr  Thr  Trp  Met  Asp  Ile  Met  Glu  Lys  His  Gly  Tyr  Gln  Thr  Gln  Lys
          115                      120                      125

Phe  Gly  Lys  Val  Asp  Tyr  Thr  Ser  Gly  His  His  Ser  Ile  Ser  Asn  Arg
     130                      135                      140

Val  Glu  Ala  Trp  Thr  Arg  Asp  Val  Ala  Phe  Leu  Leu  Arg  Gln  Glu  Gly
145                      150                      155                      160

Arg  Pro  Ile  Ile  Asn  Leu  Ile  Pro  Asp  Lys  Asn  Arg  Arg  Arg  Val  Met
                    165                      170                      175

Thr  Lys  Asp  Trp  Gln  Asn  Thr  Asp  Lys  Ala  Ile  Glu  Trp  Leu  Arg  Gln
               180                      185                      190

Val  Asn  Tyr  Thr  Lys  Pro  Phe  Val  Leu  Tyr  Leu  Gly  Leu  Asn  Leu  Pro
          195                      200                      205

His  Pro  Tyr  Pro  Ser  Pro  Ser  Ser  Gly  Glu  Asn  Phe  Gly  Ser  Ser  Thr
     210                      215                      220

Phe  His  Thr  Ser  Leu  Tyr  Trp  Leu  Glu  Lys  Val  Ala  Tyr  Asp  Ala  Ile
225                      230                      235                      240

Lys  Ile  Pro  Lys  Trp  Leu  Thr  Leu  Ser  Gln  Met  His  Pro  Val  Asp  Phe
                    245                      250                      255
```

| | | | | | | | | | | | | | | |
|---|---|---|---|---|---|---|---|---|---|---|---|---|---|---|
| Cys | Ser | Ser | Tyr 260 | Thr | Lys | Asn | Cys 265 | Thr | Gly | Lys | Phe | Thr 270 | Asn | Glu |
| Ile | Lys | Asn 275 | Ile | Arg | Ala | Phe 280 | Tyr | Ala | Met | Cys | Ala 285 | Glu | Thr | Asp |
| Ala | Met 290 | Leu | Gly | Glu | Ile 295 | Ile | Leu | Ala | Leu | His | Lys 300 | Leu | Asp | Leu |
| Gln 305 | Lys | Thr | Ile | Val 310 | Ile | Tyr | Thr | Ser | Asp | His 315 | Gly | Glu | Met | Ala | Met 320 |
| Glu | His | Arg | Gln | Phe 325 | Tyr | Lys | Met | Ser | Met 330 | Tyr | Glu | Ala | Ser | Val 335 | His |
| Val | Pro | Leu | Leu 340 | Met | Met | Gly | Pro | Gly 345 | Ile | Lys | Ala | Asn | Leu 350 | Gln | Val |
| Pro | Ser | Val 355 | Val | Ser | Leu | Val | Asp 360 | Ile | Tyr | Pro | Thr | Met 365 | Leu | Asp | Ile |
| Ala | Gly 370 | Ile | Ala | Leu | Pro | Pro 375 | Asn | Leu | Ser | Gly | Tyr 380 | Ser | Leu | Leu | Thr |
| Leu 385 | Leu | Ser | Asn | Ala | Ser 390 | Ala | Asn | Glu | Gln | Ala 395 | Phe | Lys | Phe | His | Arg 400 |
| Pro | Pro | Trp | Ile | Leu 405 | Ser | Glu | Phe | His | Gly 410 | Cys | Asn | Ala | Asn | Ala 415 | Ser |
| Thr | Tyr | Met | Leu 420 | Arg | Thr | Gly | Gln | Trp 425 | Lys | Tyr | Ile | Ala | Tyr 430 | Ala | Asp |
| Gly | Ala | Ser 435 | Val | Gln | Pro | Gln | Leu 440 | Phe | Asp | Leu | Ser | Leu 445 | Asp | Pro | Asp |
| Glu | Leu 450 | Thr | Asn | Ile | Ala | Thr 455 | Glu | Phe | Pro | Glu | Ile 460 | Thr | Tyr | Ser | Leu |
| Asp 465 | Gln | Lys | Leu | Arg | Ser 470 | Ile | Val | Asn | Tyr | Pro 475 | Lys | Val | Ser | Ala | Ser 480 |
| Val | His | Gln | Tyr | Asn 485 | Lys | Glu | Gln | Phe | Ile 490 | Met | Trp | Lys | Gln | Ser 495 | Val |
| Gly | Gln | Asn | Tyr 500 | Ser | Asn | Val | Ile | Ala 505 | His | Leu | Arg | Trp | His 510 | Gln | Asp |
| Trp | Gln | Arg 515 | Asp | Pro | Arg | Lys | Tyr 520 | Glu | Asn | Ala | Ile | Gln 525 | His | Trp | Leu |
| Thr | Ala 530 | His | Ser | Ser | Pro | Leu 535 | Ala | Ser | Ser | Pro | Thr 540 | Gln | Ser | Thr | Ser |
| Gly 545 | Ser | Gln | Pro | Thr | Leu 550 | Pro | Gln | Ser | Thr | Ser 555 | Gly |

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: Other
        (A) DESCRIPTION: linker DNA with sequence complementary
        to Sequence ID No. 4, termed "ATOS-1"

(xi) SEQUENCE DESCRIPTION: SEQ ID NO:3:

CTCTTGCTTG AATTCGGACT A         21

(2) INFORMATION FOR SEQ ID NO:4:

(i) SEQUENCE CHARACTERISTICS:
        (A) LENGTH: 25 base pairs

```
              ( B ) TYPE: nucleic acid
              ( C ) STRANDEDNESS: single
              ( D ) TOPOLOGY: linear ( i i ) MOLECULE TYPE: Other
              ( A ) DESCRIPTION: linker DNA with sequence complementary
                    to Sequence ID No. 3, termed "ATOS-2"

( x i ) SEQUENCE DESCRIPTION: SEQ ID NO:4:

TAGTCCGAAT TCAAGCAAGA GCACA                                                    25

( 2 ) INFORMATION FOR SEQ ID NO:5:

( i ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( i i ) MOLECULE TYPE: Other
              ( A ) DESCRIPTION: linker DNA with sequence complementary
                    to Sequence ID No. 6, termed "ATOS-4"

( x i ) SEQUENCE DESCRIPTION: SEQ ID NO:5:

CTCTTGCTTA AGCTTGGACT A                                                        21

( 2 ) INFORMATION FOR SEQ ID NO:6:

( i ) SEQUENCE CHARACTERISTICS:
              ( A ) LENGTH: 25 base pairs
              ( B ) TYPE: nucleic acid
              ( C ) STRANDEDNESS: single
              ( D ) TOPOLOGY: linear ( i i ) MOLECULE TYPE: Other
              ( A ) DESCRIPTION: linker DNA with sequence complementary
                    to Sequence ID No. 5, termed "ATOS-5"

( x i ) SEQUENCE DESCRIPTION: SEQ ID NO:6:

TAGTCCAAGC TTAAGCAAGA GCACA                                                    25

( 2 ) INFORMATION FOR SEQ ID NO:7:

( i ) SEQUENCE CHARACTERISTICS:
              ( A ) LENGTH: 554 amino acids
              ( B ) TYPE: amino acid
              ( D ) TOPOLOGY: linear ( i i ) MOLECULE TYPE: peptide ( x i ) SEQUENCE DESCRIPTION: SEQ ID NO:7:
```

|     | Met | Pro | Ala | Met | Leu | Leu | Leu | Val | Ser | Val | Val | Ala | Ala | Leu | Ala |
|-----|-----|-----|-----|-----|-----|-----|-----|-----|-----|-----|-----|-----|-----|-----|-----|
|     | 1   |     |     |     | 5   |     |     |     |     | 10  |     |     |     |     | 15  |
|     | Leu | Ala | Ala | Pro | Ala | Pro | Arg | Thr | Gln | Lys | Lys | Arg | Met | Gln | Val | Asn |
|     |     |     |     | 20  |     |     |     | 25  |     |     |     |     | 30  |     |     |
|     | Gln | Ala | Pro | Asn | Val | Val | Leu | Val | Ala | Ser | Asp | Ser | Phe | Asp | Gly | Arg |
|     |     |     | 35  |     |     |     |     | 40  |     |     |     | 45  |     |     |     |
|     | Leu | Thr | Phe | Gln | Pro | Gly | Ser | Gln | Val | Val | Lys | Leu | Pro | Phe | Ile | Asn |
|     |     | 50  |     |     |     |     | 55  |     |     |     |     | 60  |     |     |     |
|     | Phe | Met | Arg | Ala | His | Gly | Thr | Thr | Phe | Leu | Asn | Ala | Tyr | Thr | Asn | Ser |
|     | 65  |     |     |     | 70  |     |     |     |     | 75  |     |     |     |     | 80  |
|     | Pro | Ile | Cys | Cys | Pro | Ser | Arg | Ala | Ala | Met | Trp | Ser | Gly | Leu | Phe | Thr |
|     |     |     |     |     | 85  |     |     |     |     | 90  |     |     |     |     | 95  |
|     | His | Leu | Thr | Glu | Ser | Trp | Asn | Asn | Phe | Lys | Gly | Leu | Asp | Pro | Asn | Tyr |
|     |     |     |     | 100 |     |     |     |     | 105 |     |     |     | 110 |     |     |
|     | Thr | Thr | Trp | Met | Asp | Ile | Met | Glu | Lys | His | Gly | Tyr | Gln | Thr | Gln | Lys |

|     |     |     |     | 115 |     |     |     |     | 120 |     |     |     |     | 125 |     |     |     |     |
|-----|-----|-----|-----|-----|-----|-----|-----|-----|-----|-----|-----|-----|-----|-----|-----|-----|-----|-----|

Phe Gly Lys Val Asp Tyr Thr Ser Gly His His Ser Ile Ser Asn Arg
    130             135             140

Val Glu Ala Trp Thr Arg Asp Val Ala Phe Leu Leu Arg Gln Glu Gly
145             150             155                         160

Arg Pro Ile Ile Asn Leu Ile Pro Asp Lys Asn Arg Arg Arg Val Met
            165             170                         175

Thr Lys Asp Trp Gln Asn Thr Asp Lys Ala Ile Glu Trp Leu Arg Gln
            180             185             190

Val Asn Tyr Thr Lys Pro Phe Val Leu Tyr Leu Gly Leu Asn Pro His
    195             200             205

Pro Tyr Pro Ser Pro Ser Ser Gly Glu Asn Phe Gly Ser Ser Thr Phe
    210             215             220

His Thr Ser Leu Tyr Trp Leu Glu Lys Val Ala Tyr Asp Ala Ile Lys
225             230             235                         240

Ile Pro Lys Trp Leu Thr Leu Ser Gln Met His Pro Val Asp Phe Cys
            245             250             255

Ser Ser Tyr Thr Lys Asn Cys Thr Gly Lys Phe Thr Glu Asn Glu Ile
            260             265             270

Lys Asn Ile Arg Ala Phe Tyr Tyr Ala Met Cys Ala Glu Thr Asp Ala
            275             280             285

Met Leu Gly Glu Ile Ile Leu Ala Leu His Lys Leu Asp Leu Leu Gln
    290             295             300

Lys Thr Ile Val Ile Tyr Thr Ser Asp His Gly Glu Met Ala Met Glu
305             310             315                         320

His Arg Gln Phe Tyr Lys Met Ser Tyr Glu Ala Ser Val His Val Pro
            325             330             335

Leu Leu Met Met Gly Pro Gly Ile Lys Ala Asn Leu Gln Val Pro Ser
            340             345             350

Val Val Ser Leu Val Asp Ile Tyr Pro Thr Met Leu Asp Ile Ala Gly
            355             360             365

Ile Ala Leu Pro Pro Asn Leu Ser Gly Tyr Ser Leu Leu Thr Leu Leu
    370             375             380

Ser Asn Ala Ser Ala Asn Glu Gln Ala Phe Lys Phe His Arg Pro Pro
385             390             395                         400

Trp Ile Leu Ser Glu Phe His Gly Cys Asn Ala Asn Ala Ser Thr Tyr
            405             410             415

Met Leu Arg Thr Gly Gln Trp Lys Tyr Ile Ala Tyr Ala Asp Gly Ala
            420             425             430

Ser Val Gln Pro Gln Leu Phe Asp Leu Ser Leu Asp Pro Asp Glu Leu
            435             440             445

Thr Asn Ile Ala Thr Glu Phe Pro Glu Ile Thr Tyr Ser Leu Asp Gln
    450             455             460

Lys Leu Arg Ser Ile Val Asn Tyr Pro Lys Val Ser Ala Ser Val His
465             470             475                         480

Gln Tyr Asn Lys Glu Gln Phe Ile Met Trp Lys Gln Ser Val Gly Gln
            485             490             495

Asn Tyr Ser Asn Val Ile Ala His Leu Arg Trp His Gln Asp Trp Gln
            500             505             510

Arg Asp Pro Arg Lys Tyr Glu Asn Ala Ile Gln His Trp Leu Thr Ala
            515             520             525

His Ser Ser Pro Leu Ala Ser Ser Pro Thr Gln Ser Thr Ser Gly Ser
530             535             540

```
Gln  Pro  Thr  Leu  Pro  Gln  Ser  Thr  Ser  Gly
545                 550
```

(2) INFORMATION FOR SEQ ID NO:8:

(i) SEQUENCE CHARACTERISTICS:
    (A) LENGTH: 509 amino acids
    (B) TYPE: amino acid
    (D) TOPOLOGY: linear (ii) MOLECULE TYPE: peptide (xi) SEQUENCE DESCRIPTION: SEQ ID NO:8:

```
Met  Ser  Met  Gly  Ala  Pro  Arg  Ser  Leu  Leu  Leu  Ala  Leu  Ala  Ala  Gly
1              5                    10                       15

Leu  Ala  Val  Ala  Arg  Pro  Pro  Asn  Ile  Val  Leu  Ile  Phe  Ala  Asp  Asp
               20                    25                       30

Leu  Gly  Tyr  Gly  Asp  Leu  Gly  Cys  Tyr  Gly  His  Pro  Ser  Ser  Thr  Thr
          35                    40                       45

Pro  Asn  Leu  Asp  Gln  Leu  Ala  Ala  Gly  Gly  Leu  Arg  Phe  Thr  Asp  Phe
     50                    55                       60

Tyr  Val  Pro  Val  Ser  Leu  Cys  Thr  Pro  Ser  Arg  Ala  Ala  Leu  Leu  Thr
65                      70                    75                            80

Gly  Arg  Leu  Pro  Val  Arg  Met  Gly  Met  Tyr  Pro  Gly  Val  Leu  Val  Pro
                    85                    90                            95

Ser  Ser  Arg  Gly  Gly  Leu  Pro  Leu  Glu  Glu  Val  Thr  Val  Ala  Glu  Val
               100                      105                 110

Leu  Ala  Ala  Arg  Gly  Tyr  Leu  Thr  Gly  Met  Ala  Gly  Lys  Trp  His  Leu
          115                      120                 125

Gly  Val  Gly  Pro  Glu  Gly  Ala  Phe  Leu  Pro  Pro  His  Gln  Gly  Phe  His
     130                      135                 140

Arg  Phe  Leu  Gly  Ile  Pro  Tyr  Ser  His  Asp  Gln  Gly  Pro  Cys  Gln  Asn
145                      150                 155                           160

Leu  Thr  Cys  Phe  Pro  Pro  Ala  Thr  Pro  Cys  Asp  Gly  Gly  Cys  Asp  Gln
                    165                 170                      175

Gly  Leu  Val  Pro  Ile  Pro  Leu  Leu  Ala  Asn  Leu  Ser  Val  Glu  Ala  Gln
               180                 185                      190

Pro  Pro  Trp  Leu  Pro  Gly  Leu  Glu  Ala  Arg  Tyr  Met  Ala  Phe  Ala  His
          195                 200                      205

Asp  Leu  Met  Ala  Asp  Ala  Gln  Arg  Gln  Asp  Arg  Pro  Phe  Phe  Leu  Tyr
     210                 215                      220

Tyr  Ala  Ser  His  His  Thr  His  Tyr  Pro  Gln  Phe  Ser  Gly  Gln  Ser  Phe
225                 230                      235                           240

Ala  Glu  Arg  Ser  Gly  Arg  Gly  Pro  Phe  Gly  Asp  Ser  Leu  Met  Glu  Leu
               245                      250                      255

Asp  Ala  Ala  Val  Gly  Thr  Leu  Met  Thr  Ala  Ile  Gly  Asp  Leu  Gly  Leu
          260                      265                      270

Leu  Glu  Glu  Thr  Leu  Val  Ile  Phe  Thr  Ala  Asp  Asn  Gly  Pro  Glu  Thr
     275                      280                      285

Met  Arg  Met  Ser  Arg  Gly  Gly  Cys  Ser  Gly  Leu  Leu  Arg  Cys  Gly  Lys
     290                      295                      300

Gly  Thr  Thr  Tyr  Glu  Gly  Gly  Val  Arg  Glu  Pro  Ala  Leu  Ala  Phe  Trp
305                      310                      315                      320

Pro  Gly  His  Ile  Ala  Pro  Gly  Val  Thr  His  Glu  Leu  Ala  Ser  Ser  Leu
               325                      330                      335

Asp  Leu  Leu  Pro  Thr  Leu  Ala  Ala  Leu  Ala  Gly  Ala  Pro  Leu  Pro  Asn
          340                      345                      350
```

```
Val  Thr  Leu  Asp  Gly  Phe  Asp  Leu  Ser  Pro  Leu  Leu  Leu  Gly  Thr  Gly
          355                 360                      365

Lys  Ser  Pro  Arg  Gln  Ser  Leu  Phe  Phe  Tyr  Pro  Ser  Tyr  Pro  Asp  Glu
     370                 375                      380

Val  Arg  Gly  Val  Phe  Ala  Val  Arg  Thr  Gly  Lys  Tyr  Lys  Ala  His  Phe
385                      390                      395                      400

Phe  Thr  Gln  Gly  Ser  Ala  His  Ser  Asp  Thr  Thr  Ala  Asp  Pro  Ala  Cys
                    405                      410                      415

His  Ala  Ser  Ser  Ser  Leu  Thr  Ala  His  Glu  Pro  Pro  Leu  Leu  Tyr  Asp
               420                      425                      430

Leu  Ser  Lys  Asp  Pro  Gly  Glu  Asn  Tyr  Asn  Leu  Leu  Gly  Gly  Val  Ala
          435                      440                      445

Gly  Ala  Thr  Pro  Glu  Val  Leu  Gln  Ala  Leu  Lys  Gln  Leu  Gln  Leu  Leu
     450                      455                      460

Lys  Ala  Gln  Leu  Asp  Ala  Ala  Val  Thr  Phe  Gly  Pro  Ser  Gln  Val  Ala
465                      470                      475                      480

Arg  Gly  Glu  Asp  Pro  Ala  Leu  Gln  Ile  Cys  Cys  His  Pro  Gly  Cys  Thr
               485                      490                      495

Pro  Arg  Pro  Ala  Cys  Cys  His  Cys  Pro  Asp  Pro  His  Ala
                    500                      505
```

( 2 ) INFORMATION FOR SEQ ID NO:9:

( i ) SEQUENCE CHARACTERISTICS:
( A ) LENGTH: 583 amino acids
( B ) TYPE: amino acid
( D ) TOPOLOGY: linear ( i i ) MOLECULE TYPE: peptide ( x i ) SEQUENCE DESCRIPTION: SEQ ID NO:9:

```
Met  Pro  Leu  Arg  Lys  Met  Lys  Ile  Pro  Phe  Leu  Leu  Leu  Phe  Phe  Leu
1                   5                        10                      15

Trp  Glu  Ala  Glu  Ser  His  Glu  Ala  Ser  Arg  Pro  Asn  Ile  Ile  Leu  Val
               20                   25                      30

Met  Ala  Asp  Asp  Leu  Gly  Ile  Gly  Asp  Pro  Gly  Cys  Tyr  Gly  Asn  Lys
               35                   40                      45

Thr  Ile  Arg  Thr  Pro  Asn  Ile  Asp  Arg  Leu  Ala  Ser  Gly  Gly  Val  Lys
     50                      55                      60

Leu  Thr  Gln  His  Leu  Ala  Ala  Ser  Pro  Leu  Cys  Thr  Pro  Ser  Arg  Ala
65                       70                      75                      80

Ala  Phe  Met  Thr  Gly  Arg  Tyr  Pro  Val  Arg  Ser  Gly  Met  Ala  Ser  Trp
               85                       90                     95

Ser  Arg  Thr  Gly  Val  Phe  Leu  Phe  Thr  Ala  Ser  Ser  Gly  Gly  Leu  Pro
               100                      105                     110

Thr  Asp  Glu  Ile  Thr  Phe  Ala  Lys  Leu  Leu  Lys  Asp  Gln  Gly  Tyr  Ser
               115                      120                     125

Thr  Ala  Leu  Ile  Gly  Lys  Trp  His  Leu  Gly  Met  Ser  Cys  His  Ser  Lys
          130                      135                      140

Thr  Asp  Phe  Cys  His  His  Pro  Leu  His  His  Gly  Phe  Asn  Tyr  Phe  Tyr
145                      150                      155                      160

Gly  Ile  Ser  Leu  Thr  Asn  Leu  Arg  Asp  Cys  Lys  Pro  Gly  Glu  Gly  Ser
                    165                      170                      175

Val  Phe  Thr  Thr  Gly  Phe  Lys  Arg  Leu  Val  Phe  Leu  Pro  Leu  Gln  Ile
                    180                      185                      190

Val  Gly  Val  Thr  Leu  Leu  Thr  Leu  Ala  Ala  Leu  Asn  Cys  Leu  Gly  Leu
```

|     |     |     |     |     | 195 |     |     |     |     | 200 |     |     |     |     | 205 |     |     |
|-----|-----|-----|-----|-----|-----|-----|-----|-----|-----|-----|-----|-----|-----|-----|-----|-----|-----|

Leu His Val Pro Leu Gly Val Phe Phe Ser Leu Leu Phe Leu Ala Ala
210 215 220

Leu Ile Leu Thr Leu Phe Leu Gly Phe Leu His Tyr Phe Arg Pro Leu
225 230 235 240

Asn Cys Phe Met Met Arg Asn Tyr Glu Ile Ile Gln Gln Pro Met Ser
245 250 255

Tyr Asp Asn Leu Thr Gln Arg Leu Thr Val Glu Ala Ala Gln Phe Ile
260 265 270

Gln Arg Asn Thr Glu Thr Pro Phe Leu Leu Val Leu Ser Tyr Leu His
275 280 285

Val His Thr Ala Leu Phe Ser Ser Lys Asp Phe Ala Gly Lys Ser Gln
290 295 300

His Gly Val Tyr Gly Asp Ala Val Glu Glu Met Asp Trp Ser Val Gly
305 310 315 320

Gln Ile Leu Asn Leu Leu Asp Glu Leu Arg Leu Ala Asn Asp Thr Leu
325 330 335

Ile Tyr Phe Thr Ser Asp Gln Gly Ala His Val Glu Glu Val Ser Ser
340 345 350

Lys Gly Glu Ile His Gly Gly Ser Asn Gly Ile Tyr Lys Gly Gly Lys
355 360 365

Ala Asn Asn Trp Glu Gly Gly Ile Arg Val Pro Gly Ile Leu Arg Trp
370 375 380

Pro Arg Val Ile Gln Ala Gly Gln Lys Ile Asp Glu Pro Thr Ser Asn
385 390 395 400

Met Asp Ile Phe Pro Thr Val Ala Lys Leu Ala Gly Ala Pro Leu Pro
405 410 415

Glu Asp Arg Ile Ile Asp Gly Arg Asp Leu Met Pro Leu Leu Glu Gly
420 425 430

Lys Ser Gln Arg Ser Asp His Glu Phe Leu Phe His Tyr Cys Asn Ala
435 440 445

Tyr Leu Asn Ala Val Arg Trp His Pro Gln Asn Ser Thr Ser Ile Trp
450 455 460

Lys Ala Phe Phe Phe Thr Pro Asn Phe Asn Pro Val Gly Ser Asn Gly
465 470 475 480

Cys Phe Ala Thr His Val Cys Phe Cys Phe Gly Ser Tyr Val Thr His
485 490 495

His Asp Pro Pro Leu Leu Phe Asp Ile Ser Lys Asp Pro Arg Glu Arg
500 505 510

Asn Pro Leu Thr Pro Ala Ser Glu Pro Arg Phe Tyr Glu Ile Leu Lys
515 520 525

Val Met Gln Glu Ala Ala Asp Arg His Thr Gln Thr Leu Pro Glu Val
530 535 540

Pro Asp Gln Phe Ser Trp Asn Asn Phe Leu Trp Lys Pro Trp Leu Gln
545 550 555 560

Leu Cys Cys Pro Ser Thr Gly Leu Ser Cys Gln Cys Asp Arg Glu Lys
565 570 575

Gln Asp Lys Arg Leu Ser Arg
580

( 2 ) INFORMATION FOR SEQ ID NO:10:

( i ) SEQUENCE CHARACTERISTICS:
( A ) LENGTH: 533 amino acids
( B ) TYPE: amino acid ( D ) TOPOLOGY: linear ( i i ) MOLECULE TYPE: peptide ( x i ) SEQUENCE DESCRIPTION: SEQ ID NO:10:

| Met | Gly | Pro | Arg | Gly | Ala | Ala | Ser | Leu | Pro | Arg | Gly | Pro | Gly | Arg |
|---|---|---|---|---|---|---|---|---|---|---|---|---|---|---|
| 1 | | | | 5 | | | | | 10 | | | | | 15 |
| Arg | Leu | Leu | Leu | Pro | Val | Val | Leu | Pro | Leu | Leu | Leu | Leu | Leu | Leu |
| | | | 20 | | | | 25 | | | | | 30 | | |
| Ala | Pro | Pro | Gly | Ser | Gly | Ala | Gly | Ala | Ser | Arg | Pro | Pro | His | Leu | Val |
| | | 35 | | | | 40 | | | | | 45 | | | |
| Phe | Leu | Leu | Ala | Asp | Asp | Leu | Gly | Trp | Asn | Asp | Val | Gly | Phe | His | Gly |
| | 50 | | | | | 55 | | | | | 60 | | | |
| Ser | Arg | Ile | Arg | Thr | Pro | His | Leu | Asp | Ala | Leu | Ala | Ala | Gly | Gly | Val |
| 65 | | | | | 70 | | | | 75 | | | | | | 80 |
| Leu | Leu | Asp | Asn | Tyr | Tyr | Thr | Gln | Pro | Leu | Cys | Thr | Pro | Ser | Arg | Ser |
| | | | | 85 | | | | | 90 | | | | | 95 | |
| Gln | Leu | Leu | Thr | Gly | Arg | Tyr | Gln | Ile | Arg | Thr | Gly | Leu | Gln | His | Gln |
| | | | 100 | | | | | 105 | | | | | 110 | | |
| Ile | Ile | Trp | Pro | Cys | Gln | Pro | Ser | Cys | Val | Pro | Leu | Asp | Glu | Lys | Leu |
| | | 115 | | | | | 120 | | | | | 125 | | | |
| Leu | Pro | Gln | Leu | Leu | Lys | Glu | Ala | Gly | Tyr | Thr | Thr | His | Met | Val | Gly |
| | 130 | | | | | 135 | | | | | 140 | | | | |
| Lys | Trp | His | Leu | Gly | Met | Tyr | Arg | Lys | Glu | Cys | Leu | Pro | Thr | Arg | Arg |
| 145 | | | | | 150 | | | | | 155 | | | | | 160 |
| Gly | Phe | Asp | Thr | Tyr | Phe | Gly | Tyr | Leu | Leu | Gly | Ser | Glu | Asp | Tyr | Tyr |
| | | | | 165 | | | | | 170 | | | | | 175 | |
| Ser | His | Glu | Arg | Cys | Thr | Leu | Ile | Asp | Ala | Leu | Asn | Val | Thr | Arg | Cys |
| | | | 180 | | | | | 185 | | | | | 190 | | |
| Ala | Leu | Asp | Phe | Arg | Asp | Gly | Glu | Glu | Val | Ala | Thr | Gly | Tyr | Lys | Asn |
| | | 195 | | | | | 200 | | | | | 205 | | | |
| Met | Tyr | Ser | Thr | Asn | Ile | Phe | Thr | Lys | Arg | Ala | Ile | Ala | Leu | Ile | Thr |
| | 210 | | | | | 215 | | | | | 220 | | | | |
| Asn | His | Pro | Pro | Glu | Lys | Pro | Leu | Phe | Leu | Tyr | Leu | Ala | Leu | Gln | Ser |
| 225 | | | | | 230 | | | | | 235 | | | | | 240 |
| Val | His | Glu | Pro | Leu | Gln | Val | Pro | Glu | Glu | Tyr | Leu | Lys | Pro | Tyr | Asp |
| | | | | 245 | | | | | 250 | | | | | 255 | |
| Phe | Ile | Gln | Asp | Lys | Asn | Arg | His | His | Tyr | Ala | Gly | Met | Val | Ser | Leu |
| | | | 260 | | | | | 265 | | | | | 270 | | |
| Met | Asp | Glu | Ala | Val | Gly | Asn | Val | Thr | Ala | Ala | Leu | Lys | Ser | Ser | Gly |
| | | 275 | | | | | 280 | | | | | 285 | | | |
| Leu | Trp | Asn | Asn | Thr | Val | Phe | Ile | Phe | Ser | Thr | Asp | Asn | Gly | Gly | Gln |
| | 290 | | | | | 295 | | | | | 300 | | | | |
| Thr | Leu | Ala | Gly | Gly | Asn | Asn | Trp | Pro | Leu | Arg | Gly | Arg | Lys | Trp | Ser |
| 305 | | | | | 310 | | | | | 315 | | | | | 320 |
| Leu | Trp | Glu | Gly | Gly | Val | Arg | Gly | Val | Gly | Phe | Val | Ala | Ser | Pro | Leu |
| | | | | 325 | | | | | 330 | | | | | 335 | |
| Leu | Lys | Gln | Lys | Gly | Val | Lys | Asn | Arg | Glu | Leu | Ile | His | Ile | Ser | Asp |
| | | | 340 | | | | | 345 | | | | | 350 | | |
| Trp | Leu | Pro | Thr | Leu | Val | Lys | Leu | Ala | Arg | Gly | His | Thr | Asn | Gly | Thr |
| | | 355 | | | | | 360 | | | | | 365 | | | |
| Lys | Pro | Leu | Asp | Gly | Phe | Asp | Met | Trp | Lys | Thr | Ile | Ser | Glu | Gly | Ser |
| | 370 | | | | | 375 | | | | | 380 | | | | |
| Pro | Ser | Pro | Arg | Ile | Glu | Leu | Leu | His | Asn | Ile | Asp | Pro | Asn | Phe | Val |
| 385 | | | | | 390 | | | | | 395 | | | | | 400 |

```
Asp  Ser  Ser  Pro  Cys  Pro  Arg  Asn  Ser  Met  Ala  Pro  Ala  Lys  Asp  Asp
                    405                      410                     415

Ser  Ser  Leu  Pro  Glu  Tyr  Ser  Ala  Phe  Asn  Thr  Ser  Val  His  Ala  Ala
                    420                      425                     430

Ile  Arg  His  Gly  Asn  Trp  Lys  Leu  Leu  Thr  Gly  Tyr  Pro  Gly  Cys  Gly
          435                     440                          445

Tyr  Trp  Phe  Pro  Pro  Pro  Ser  Gln  Tyr  Asn  Val  Ser  Glu  Ile  Pro  Ser
     450                      455                     460

Ser  Asp  Pro  Pro  Thr  Lys  Thr  Leu  Trp  Leu  Phe  Asp  Ile  Asp  Arg  Asp
465                      470                     475                          480

Pro  Glu  Glu  Arg  His  Asp  Leu  Ser  Arg  Glu  Tyr  Pro  His  Ile  Val  Thr
                    485                      490                          495

Lys  Leu  Leu  Ser  Arg  Leu  Gln  Phe  Tyr  His  Lys  His  Ser  Val  Pro  Val
               500                      505                     510

Tyr  Phe  Pro  Ala  Gln  Asp  Pro  Arg  Cys  Asp  Pro  Lys  Ala  Thr  Gly  Val
          515                      520                     525

Trp  Gly  Pro  Trp  Met
     530
```

( 2 ) INFORMATION FOR SEQ ID NO:11:

( i ) SEQUENCE CHARACTERISTICS:
( A ) LENGTH: 45 amino acids
( B ) TYPE: amino acid
( D ) TOPOLOGY: linear ( i i ) MOLECULE TYPE: peptide ( x i ) SEQUENCE DESCRIPTION: SEQ ID NO:11:

```
Leu  Arg  Pro  Asp  Gly  Pro  Gly  Cys  Pro  Ser  Arg  Gly  Gly  Tyr  Thr  Gly
1                   5                        10                      15

Lys  Thr  Ala  Pro  Leu  His  Phe  Asp  Gly  Leu  Thr  Asp  Gly  Lys  Glu  Pro
               20                       25                      30

Asp  Pro  Thr  Ala  Gly  Leu  Asp  Asp  Pro  Glu  Leu  Gln  Pro
```